United States Patent
Discko, Jr.

(10) Patent No.: US 7,331,450 B2
(45) Date of Patent: Feb. 19, 2008

(54) DENTAL APPLICATOR HOLDING AND MATERIAL DISPENSING TRAY

(75) Inventor: John J. Discko, Jr., Trumbull, CT (US)

(73) Assignee: Centrix, Inc., Shelton, CT (US)

( * ) Notice: Subject to any disclaimer, the term of this patent is extended or adjusted under 35 U.S.C. 154(b) by 14 days.

(21) Appl. No.: 10/999,777

(22) Filed: Nov. 30, 2004

(65) Prior Publication Data

US 2006/0115315 A1    Jun. 1, 2006

(51) Int. Cl.
*A61B 19/02* (2006.01)
*A61C 3/00* (2006.01)
*B65D 1/36* (2006.01)

(52) U.S. Cl. ............ 206/63.5; 206/369; 206/563; 433/77; 433/163

(58) Field of Classification Search .............. 206/63.5, 206/362–362.4, 369–370, 438, 443, 562–564; 211/60.1, 74; 433/77–80, 90, 163; 132/317–318, 132/321–329
See application file for complete search history.

(56) References Cited

U.S. PATENT DOCUMENTS

| | | | |
|---|---|---|---|
| 4,892,481 A * | 1/1990 | Kopunek et al. | 206/562 |
| 5,033,629 A * | 7/1991 | Caine | 211/69.5 |
| 5,106,297 A | 4/1992 | Discko, Jr. | |
| 5,199,567 A | 4/1993 | Discko, Jr. | |
| 5,377,823 A * | 1/1995 | Steen et al. | 206/63.5 |
| 5,538,134 A * | 7/1996 | Pitesky | 206/438 |
| 5,660,273 A | 8/1997 | Discko, Jr. | |
| 5,749,730 A | 5/1998 | Johnsen et al. | |
| 6,202,897 B1 * | 3/2001 | Martin et al. | 206/63.5 |
| RE37,535 E * | 2/2002 | Avery et al. | 206/362.2 |
| 6,971,879 B2 * | 12/2005 | Discko, Jr. | 433/163 |
| 7,066,329 B2 * | 6/2006 | Riley | 206/443 |

* cited by examiner

*Primary Examiner*—Bryon P Gehman
(74) *Attorney, Agent, or Firm*—Fattihene & Fattibene; Paul A. Fattibene; Arthur T. Fattibene

(57) ABSTRACT

A tray for dispensing a material to be applied with an applicator having a plurality of applicator support openings. The applicator support openings have a depth and width sufficient so that when an applicator is placed therein, it is held substantially upright. The material and applicator support wells may be funnel shaped. The relatively deep narrow funnel shape protects the material placed therein from ambient light, contamination, evaporation, and spilling. The invention is particularly well suited to use in a dental procedure that may require the application of multiple different materials or materials that react with one another or that are light activated. The plurality of different material wells are readily identifiable and keep the different materials separate and ready for use.

6 Claims, 6 Drawing Sheets

DENTAL APPLICATOR HOLDING AND MATERIAL DISPENSING TRAY

FIELD OF THE INVENTION

The present invention relates in general to dispensing liquid materials to be applied with an applicator, and more particularly to a tray having openings shaped to hold an applicator.

BACKGROUND OF THE INVENTION

Applicators are often used to apply a variety of different materials. The applicators generally consist of a brush, foam, or flocking material applied to the tip or end of a handle. The applicator is often dipped into a bulk container holding the material to be applied. Often, once the material is applied to the applicator, the applicator must continue to be held to prevent contamination of the end of the applicator and applied material. In some applications of materials, such as dental materials, a first liquid material may be applied and then a second liquid material may be applied over the first. These two materials then react to produce a desired result. In applications using multiple applications of materials, it is necessary to use several different applicators. It is difficult to hold multiple applicators so as to prevent their contamination while applying the different materials.

Additionally, some time may elapse between the application of the materials, resulting in the materials being exposed to the environment between applications. Many materials may be light sensitive or have solvents that readily evaporate, therefore degrading the material between applications.

There are a large number of different trays and pallets adapted to hold a material prior to being applied with an applicator. In many of the trays used in dispensing a material, the depressions used to contain the material are often relatively wide and shallow. This renders the material to be exposed to light and air and makes it prone to spilling or evaporation. One such prior dispensing tray is disclosed in U.S. Pat. No. 5,106,297 entitled Dental Bonding Liquid and Sealant Tray issuing on Apr. 21, 1992, to John Discko, Jr. Therein disclosed is a dental tray with depressions for holding a bottle of dental material upside down and a plurality of distinctively shaped wells to receive the liquid material from the bottles. Another tray having material wells used in combination with an applicator for dispensing the material is disclosed in U.S. Pat. No. 5,660,273 entitled Single Patient Dose Medicament Dispenser With Applicator, issuing to John J. Discko, Jr. on Aug. 26, 1997.

While the prior trays utilized for dispensing materials have been beneficial in many applications, they can not hold an applicator once use has been initiated and the material has been applied. Additionally, once material has been placed in the relatively wide shallow well, the working time of the material is relatively short due to the exposure to air and light. Therefore, there is a need for a convenient, inexpensive material dispensing system that can hold and protect a material and hold an applicator in a position ready for use.

SUMMARY OF THE INVENTION

The present invention comprises a tray having a plurality of openings therein. The openings may hold a liquid to be dispensed. The openings are also adapted to hold an applicator in an upright position ready for use. In one embodiment, a tray is formed with a plurality of deep material wells and a plurality of applicator support openings. The applicator support openings have a sufficiently small opening so as to permit the applicator to be placed therein and stand upright in a self-supported position.

In another embodiment, the tray has a plurality of funnel shaped material wells that may hold a material and also act as an applicator support opening so as to hold the applicator in an upright position. Material may be placed in the tubular portion of the funnel shaped material well. The applicator, when placed within the funnel shaped material well, stands in a self-supported, upright position, resting against the bottom and walls of the funnel shaped material well. The applicator also acts as a stopper, to protect the material from ambient light and evaporation.

Accordingly, it is an object of the present invention to efficiently dispense a material, such as a gel or liquid, while protecting the material from ambient light, evaporation, or contamination.

It is a further object of the present invention to hold an applicator in an upright position ready for use.

It is an advantage of the present invention that small quantities of liquid pool at the bottom of a narrow material well, permitting efficient use of the liquid material.

It is an advantage of the present invention that the narrow, deep material well protects the material from ambient light and contamination and limits evaporation.

It is a further advantage of the present invention that an applicator is held within an applicator support opening in an upright position ready for grasping and use.

It is yet a further advantage of the present invention that it is spill proof, and that the tray may be inverted without the material contained within the relatively deep narrow wells spilling out.

It is a feature of the present invention that the in one embodiment the applicator support opening is funnel shaped.

It is a further feature of the present invention that in one embodiment the walls of the applicator support opening are sufficiently tapered to hold an applicator in an upright position without falling over.

These and other objects, advantages, and features will become readily apparent in view of the following, more detailed description.

DETAILED DESCRIPTION OF THE PREFERRED EMBODIMENTS

Figure 1:
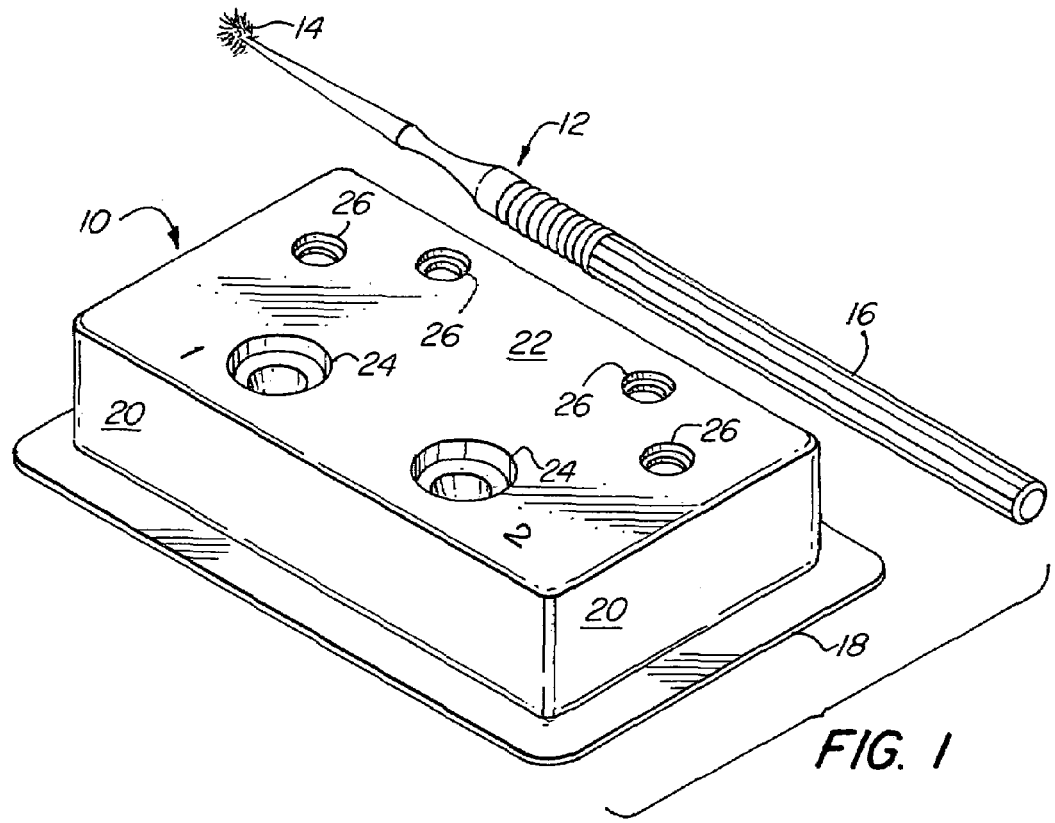
FIG. 1 is a perspective view illustrating an embodiment of the material dispensing system of the present invention.

FIG. 1 is a perspective view illustrating an embodiment of the material dispensing system. Tray 10 is used in combination with an applicator 12. The applicator 12 has an applicator portion 14, which may be made of any absorbent material such as flock, bristle brushes, foam or other material utilized in applying a liquid or other flowable material. The applicator 12 has a handle portion 16. The tray 10 has a base flange 18 and side walls 20 extending up to a top planar surface 22. Formed within the top planar surface 22 are a plurality of material wells 24 and applicator support openings 26. Preferably, tray 10 is vacuum formed from a thin plastic sheet. Alternatively, tray 10 may be injection molded from any suitable plastic material. Tray 10 can be made relatively inexpensively so as to be disposable.

Figure 2:
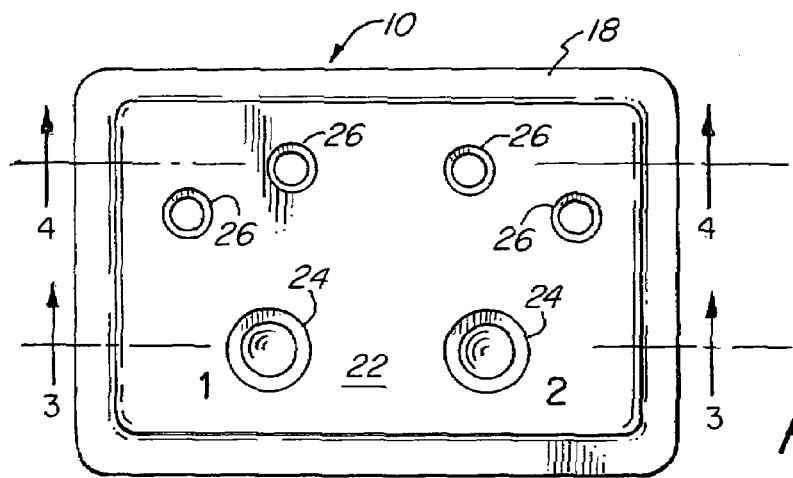
FIG. 2 is a plan view of the embodiment illustrated in FIG. 1.

FIG. 2 is a plan view, more clearly illustrating a plurality of material wells 24 and applicator support openings 26. While four applicator support openings 26 are illustrated, any number may be used. Similarly, any number of material wells 24 may be used.

Figure 3:
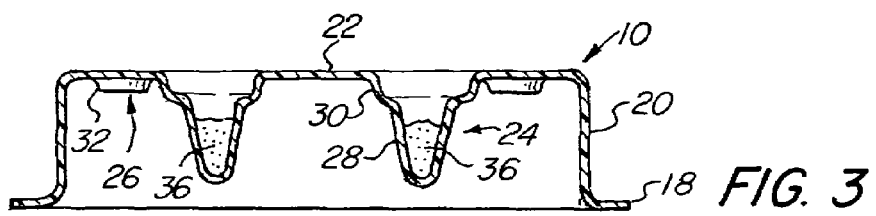
FIG. 3 is a cross section taken along line 3-3 in FIG. 2.

FIG. 3 is a cross section taken along lines 3-3 in FIG. 2. FIG. 3 more clearly illustrates the shape of the material wells 24. The material wells 24 have a relatively deep narrow structure comprised of tapered wall 28 and ledge 30. The ledge 30 provides for a larger diameter opening on the top planar surface 22. A liquid or a flowable material 36 that is to be applied may be more easily placed within the material well 24. The relatively narrow material wells 24 help protect the material 36 therein from ambient light, contamination, or from spilling. If the tapered walls 28 are sufficiently narrow, the material 36 contained therein may be prevented from falling out even when the tray 10 is inverted or turned upside down. This is due to the relatively small exposed surface area and surface tension of the material 36. Therefore, the tray 10 of the present invention is extremely spill resistant. FIG. 3 also better illustrates the applicator support openings 26. The applicator support openings 26 have a ledge or depression 32 which aids in the placement of the applicator 12, illustrated in FIG. 1, into the applicator support opening 26. The applicator support opening 26 is open to the interior of the tray 10.

Figure 4:
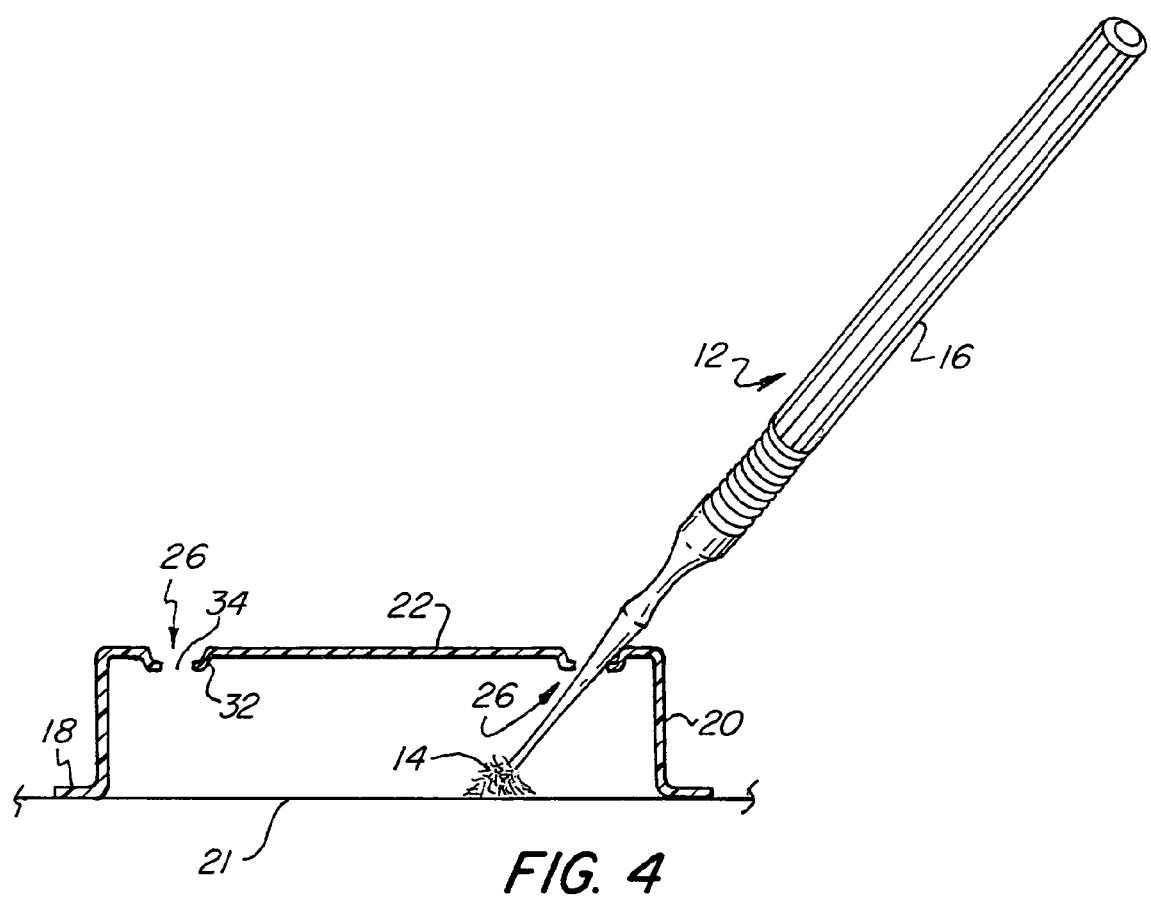
FIG. 4 is a cross section taken along line 4-4 in FIG. 2 and illustrating an applicator held in an upright position.

FIG. 4 is a cross section taken along line 4-4 in FIG. 3 and includes an applicator 12 placed within an applicator support opening 26. FIG. 4 illustrates the generally upright position of the applicator 12 as it is supported by the edges of the applicator support opening 26 and a bottom surface 21. By the term upright position of the applicator 12 it is meant that the applicator handle portion 16 is not resting on a surface and the applicator handle portion is in a position ready to be grasped. The bottom surface 21 may be any surface on which the tray 10 is placed or the bottom surface 21 may be formed from a membrane stretched across the bottom of the tray 10 and attached to the base flange 18.

The use of the material dispensing system illustrated in FIGS. 1-4 of this embodiment can readily be appreciated. A small quantity of material may be placed in either of the numbered material wells 24. A plurality of material wells 24 are provided to permit the use of materials that have separate components that react when combined or materials that require sequential application for a particular procedure. The material wells 24 have relatively steep tapered walls 28. Therefore, only a very small quantity of material is needed for providing a depth of material sufficient to submerge the applicator portion 14 therein. This is advantageous in view of the relatively high cost of many materials, such as dental materials used in different dental procedures. The dental materials used with the present invention may be bonding agents, adhesives, acids, desensitizers, as well as solvents used in different procedures such as acetone or alcohol, or any other material. The applicator 12 may be conveniently stored in an upright position by placing the applicator end 14 through the applicator support openings 26 in the top planar surface 21 of tray 10. In this way, the applicator 12 is conveniently held in an upright position so as to be easily grabbed by the user, dentist, or dental assistant. Multiple applicators 12 may be placed in the different applicator support openings 26 so as to be readily available for use. The applicator support openings 26 may be grouped adjacent a respective material well 24 so as to readily identify its use with respect to the closest material well 24. This prevents the possibility of cross contamination of materials held within the different material wells 24.

Figure 5:
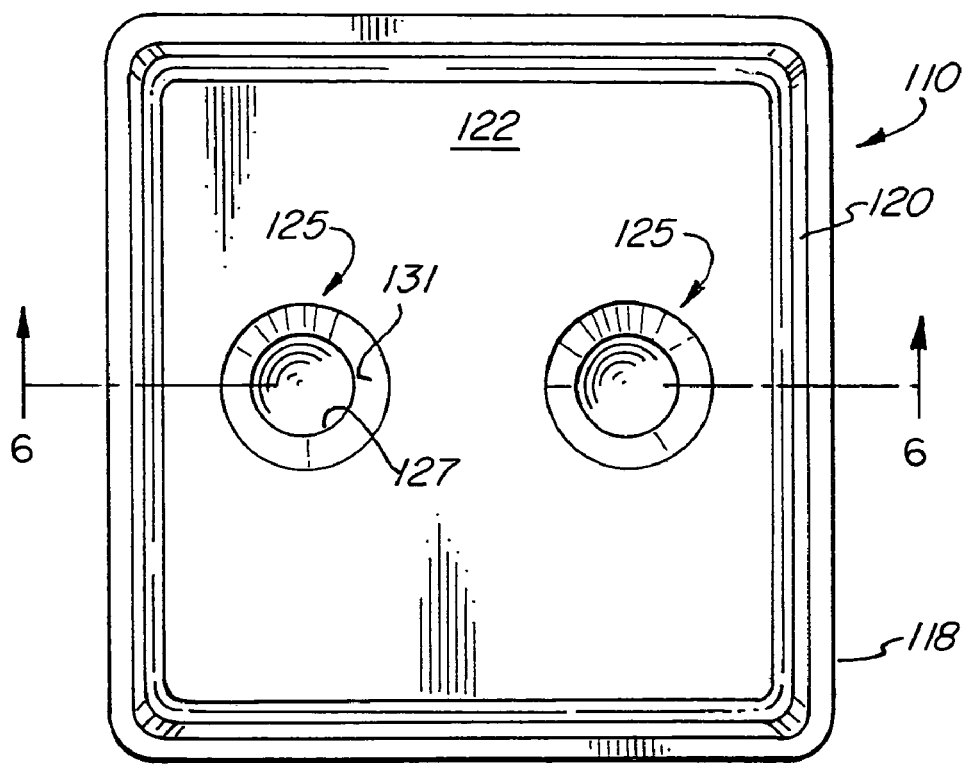
FIG. 5 is a plan view illustrating another embodiment of the present invention.

FIG. 5 is a plan view illustrating another embodiment of the present invention. Tray 110 has a base flange 118 attached to side walls 120. The side walls 120 extend upward to a top planar surface 122. The side walls 120 may be angled or tapered inward slightly. Formed within the top planar surface 122 are a plurality of material and applicator support wells 125. The material and applicator support wells 125 are funnel shaped and have a conical opening 131 and a tubular material well 127. The tubular material well 127 may be of a slight conical shape with slightly angled sidewalls.

Figure 6:
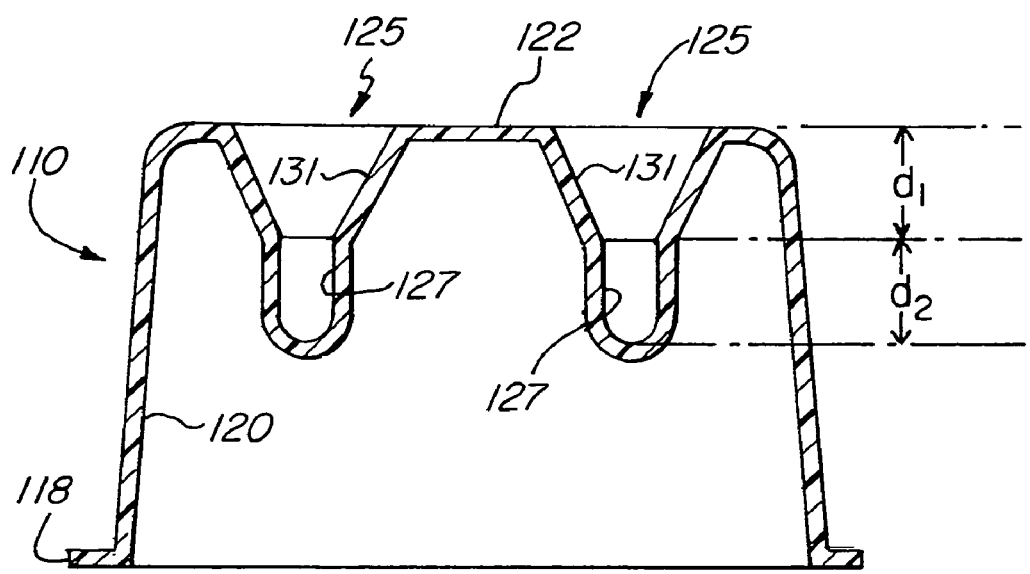
FIG. 6 is a cross section taken along line 6-6 in FIG. 5.

FIG. 6 is a cross section taken along line 6-6 in FIG. 5. FIG. 6 more clearly illustrates the funnel shape of the material and applicator support wells 125. The funnel shaped material applicator support wells 125 are formed by a conical opening 131 having a relatively broad conical structure and a narrower tubular material well 127. The narrower tubular material well 127 may have a very slight conical shape. The tubular material well 127 has an axial length of $d_2$. The conical opening 131 has an axial length of $d_1$. The combined axial length of the material and applicator support wells is $d_1$ plus $d_2$. The conical opening 131, in combination with the tubular material well 127, functions to hold the material to be applied as well as provide support for the applicator to stand substantially upright. The combination of lateral width and combined axial length of the material and applicator support wells must be sufficient so as to permit an applicator to stand substantially upright when placed therein.

Figure 7:
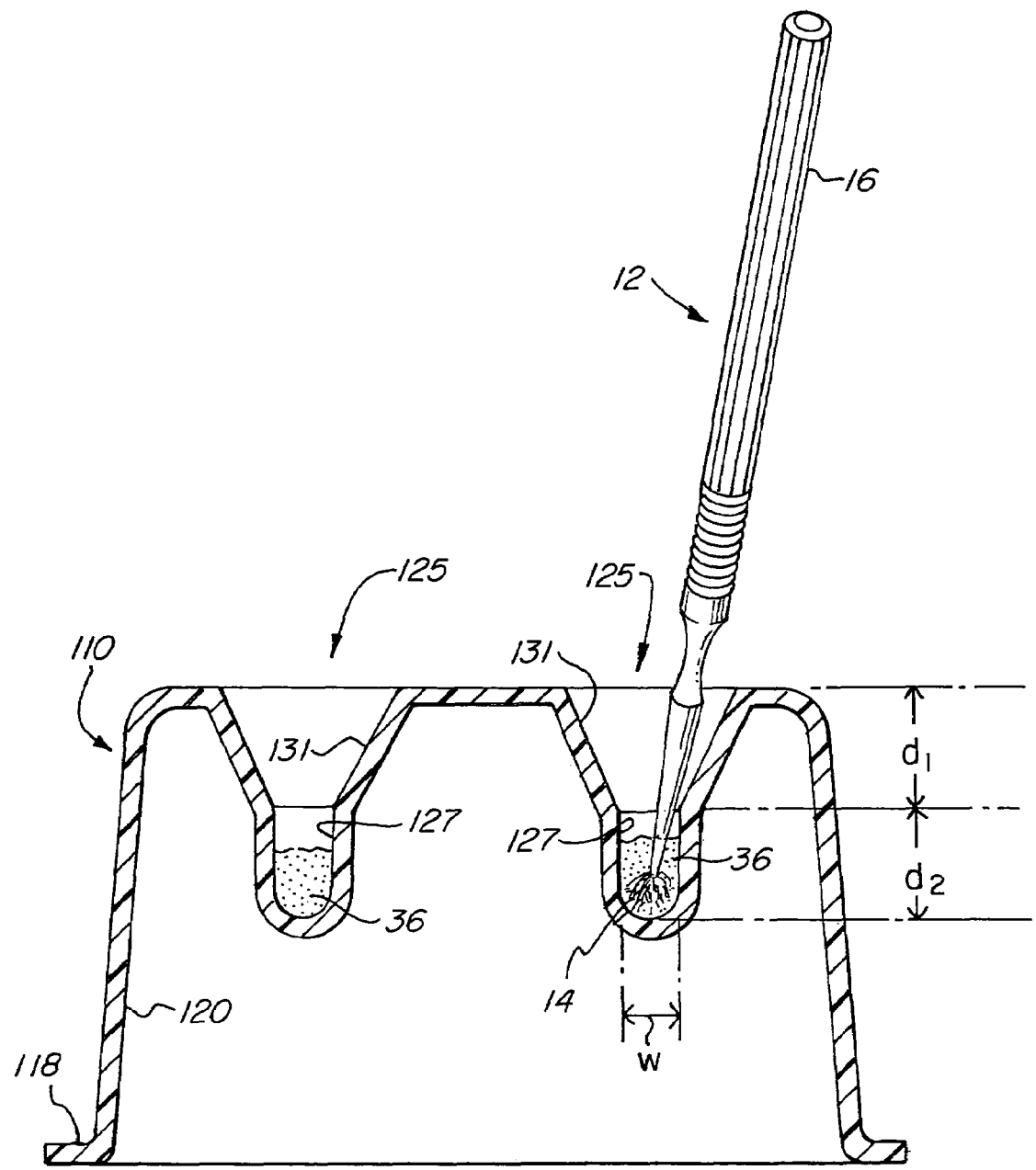
FIG. 7 is a cross section illustrating the relationship between a funnel shaped applicator support opening and an applicator held in an upright position.

FIG. 7 is a cross section schematically illustrating the tray 110 in combination with an applicator 12. A material 36 is placed within the tubular material well 127. The tubular material well 127 has a lateral width w. The lateral width w is substantially less than the axial distance $d_1$. The lateral width w may range from being substantially equal to the lateral dimension of the applicator end 14 to a multiple of three times the lateral dimension of the applicator end 14. The combined axial distance of the conical opening 131 distance $d_1$ and the axial distance $d_2$ of the tubular material well 127 is sufficient so as to permit the applicator 12 to stand upright when the applicator portion 14 is placed within the tubular material well 127. The applicator 12 is supported by a portion of the conical opening 131 and a portion of the tubular material well 127 so as to prevent the applicator 12 from falling out of the material and applicator support wells 125. The applicator 12 may therefore be left in position within the material and applicator support wells 125, ready to be easily picked up by the user and used. A portion of the handle adjacent the applicator portion 14 of the applicator 12 also aids in blocking a portion of the open end of the tubular material well 127, preventing ambient light, contamination, or air from reacting with the material 36 contained therein. This greatly prolongs the working time of the material or the time over which the material can be used in a particular procedure. The narrow lateral dimension of the tubular material well 127 also aids in preventing ambient light, contamination, or air from reacting with the material 36 contained therein.

Figure 8:
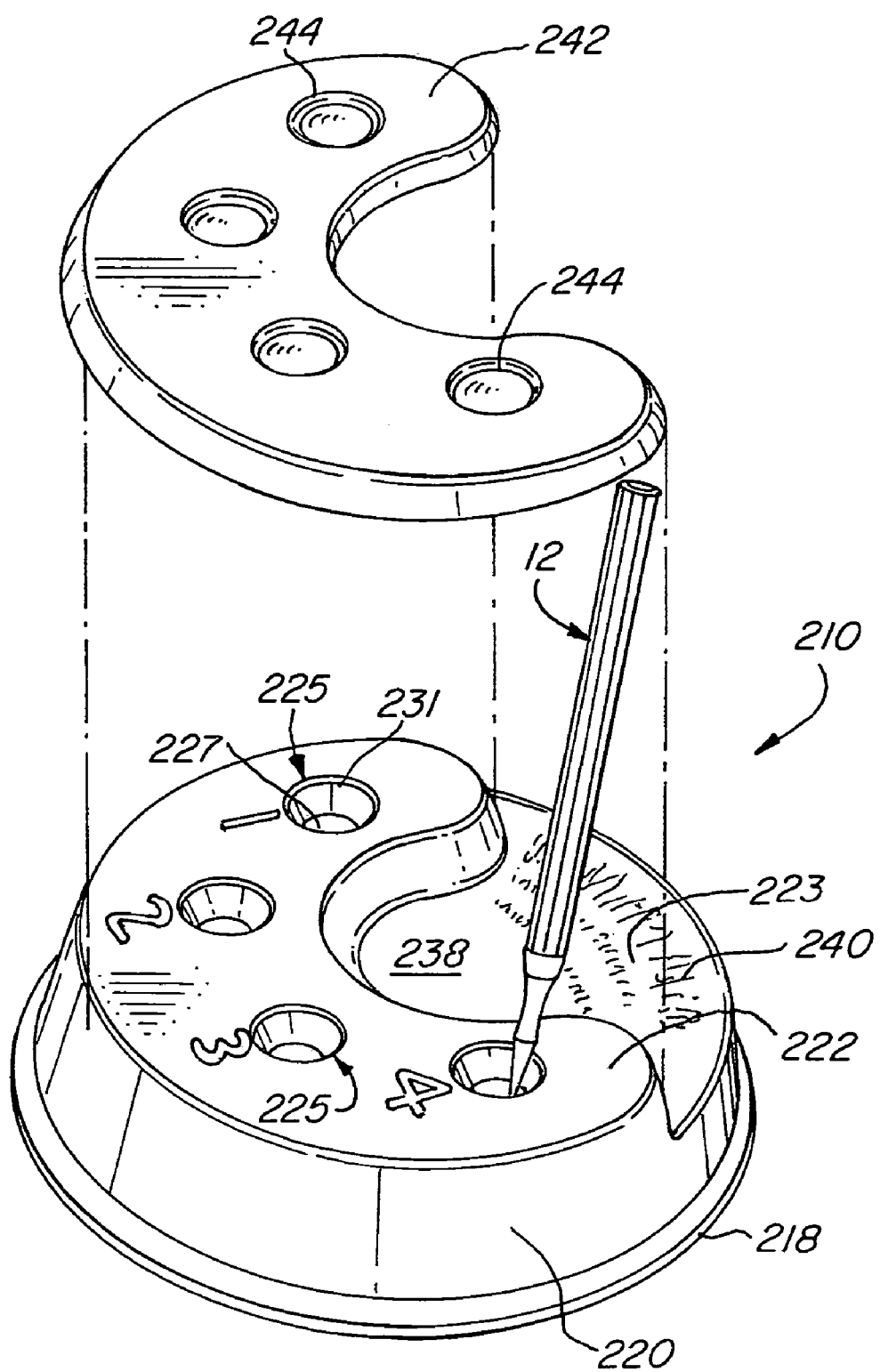
FIG. 8 is a perspective view of yet another embodiment of the present invention.

FIG. 8 illustrates another embodiment of the present invention having a distinctive shape that results in an angular orientation that is readily identifiable so as to prevent misidentification of the different wells. The material dispensing system of this embodiment comprises a tray 210 having a base flange 218 and side walls 220 extending upward. The side walls 220, in one portion, extend upward to a top planar surface 222 and in another portion, to a lower planar surface 223. The lower planar surface 223 may have indicia 240 placed thereon, as well as a thumb recess 238. Formed within the top planar surface 222 is a plurality of material and applicator support wells 225. The material and applicator support wells 225 are funnel shaped and have a conical opening 231 and a tubular material well 227. The four material and applicator support wells 225 may have identifying indicia such as numbers or letters associated therewith. An applicator 12 may be placed in any of the material and applicator support wells 225. When an applicator 12 is not placed in any of the material and applicator support wells 225, a cover 242 may be placed over the top planar surface 222. The cover 242 may have dimples 244 placed therein to better seal the material and applicator support wells 225. The cover 242 may be made of an opaque material or of an actinic material which may be orange in color that blocks the wavelength of light rays or radiation that may react with certain light sensitive materials.

Figure 9:
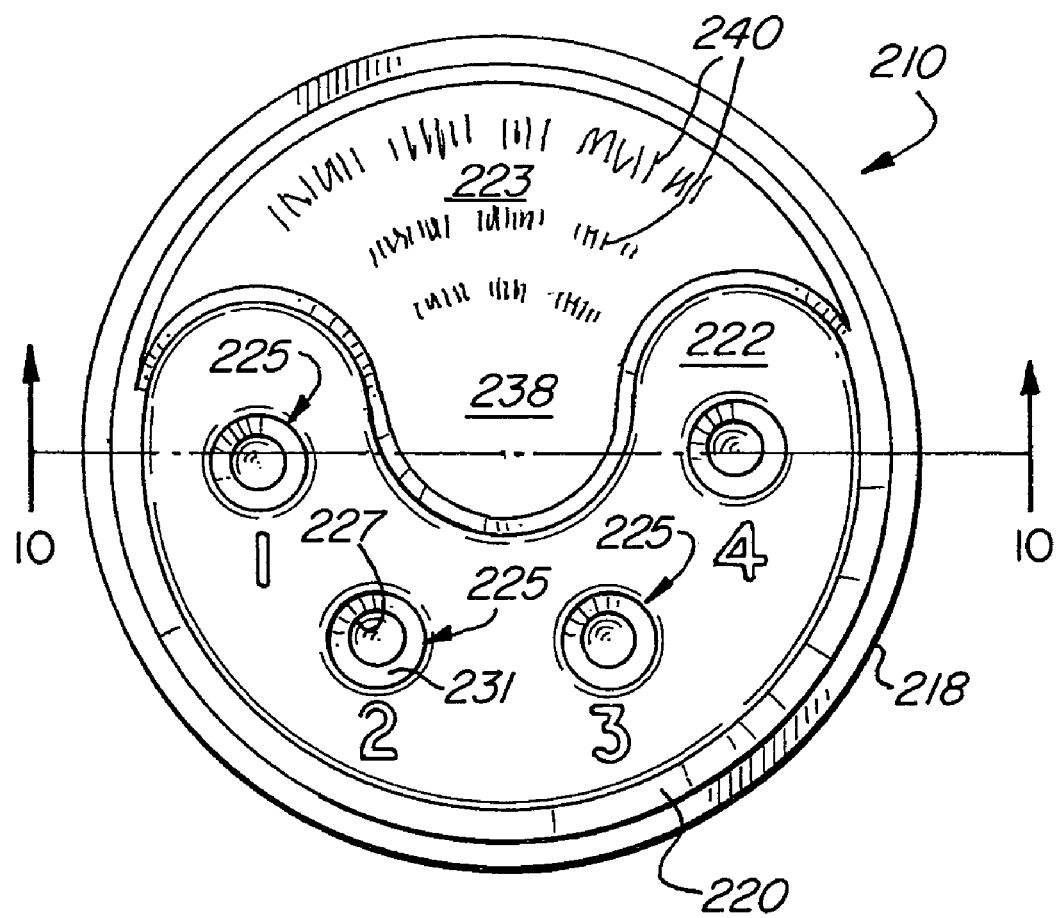
FIG. 9 is a plan view of the embodiment illustrated in FIG. 8.

FIG. 9 is a plan view more clearly illustrating the top surface of tray 210. The U-shape of the top planar surface 222 makes the relative position of the material and applicator support wells 225 more easily identifiable. As a result identification of the material in the applicator and support wells 225 may be quickly made. This reduces the possibility of the inadvertent rotation of the tray 210 and the possible resulting confusion, of which of the material and applicator support wells 225 contain the desired material. Additionally, a thumb recess 238 is formed within the U-shaped top planar surface 222, permitting easy and ergonomical grasping of the lower planar surface 223 between the thumb and fingers. Additionally, the lower planar surface 223 provides a convenient location to print identifying or informative indicia 240.

Figure 10:
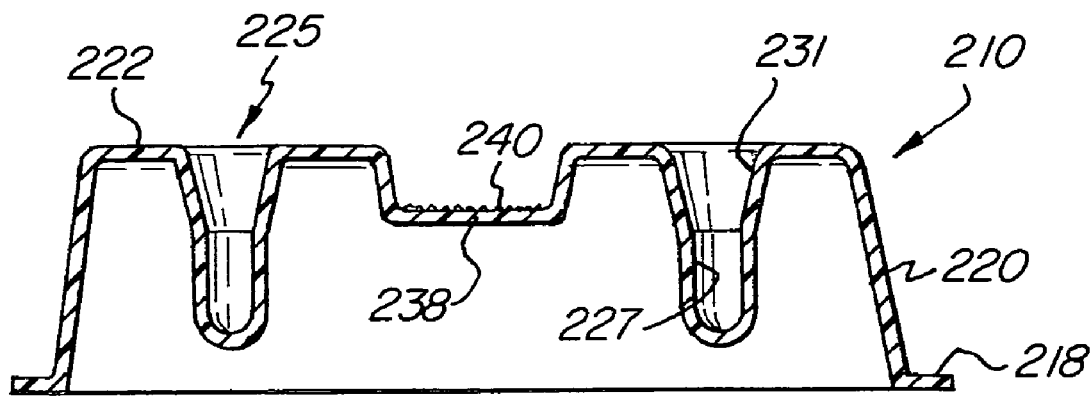
FIG. 10 is a cross sectional view taken along line 10-10 in FIG. 9.

FIG. 10 is a cross section taken along line 10-10 in FIG. 9. FIG. 10 more clearly illustrates the material and applicator support wells 225. The material and applicator support wells 225 have an axial depth and lateral width ratio sufficient so that an applicator, when placed therein, will be held substantially upright in a position that is easily grasped and that prevents contamination or contact of the applicator end to any potentially contaminated surface.

The funnel shape of the material and applicator support wells of the present invention greatly improves the dispensing of a liquid material. The material and applicator support wells are sufficiently tapered so that an applicator can be held upright when either straight or bent. Additionally, they provide a sufficient taper so that a liquid material contained therein does not fall out when inverted. The material and applicator support wells also are sufficiently deep so that the liquid contained therein is not affected by light should the material be light activated. The material and applicator support wells should also be sufficiently narrow so as to minimize or prevent evaporation of any solvents contained within the material to be applied. The material from which the trays of the present invention are made may be opaque or a transparent or translucent material capable of blocking actinic light, if the material to be used therein is light activated.

The material and applicator support wells of the present invention are arranged in a single line or curved row in a left to right arrangement. This eliminates confusion when an applicator is returned to a material and applicator support well. Other trays tried to eliminate the confusion by making the wells in different shapes, or by imprinting a color or alpha-numeric code next to a well. Placing the material and applicator support wells in a single row results in much more intuitive identification of the desired material and applicator support well position.

Additionally, the asymmetrical shape of the embodiment illustrated in FIGS. 8-10 reduces the likelihood of inadvertently misidentifying a desired material and applicator support well. Even if the tray is turned sideways or backwards, the position of the desired material and applicator support well is easily identified.

Therefore, the present invention provides for a convenient, relatively inexpensive, and easy to manufacture system for dispensing liquid or other flowable materials with an applicator. The material dispensing system of the present invention is particularly well suited to applying small quantities of material that may be used in multiple parts or applications and that react with each other or that may need to be sequentially applied in a particular procedure, or that are light activated. In the asymmetrical configuration of the material and applicator support wells, the applicator is very easily grasped for quick and convenient use.

While several embodiments of the present invention have been illustrated and described, it should be readily appreciated that various modifications may be made without departing from the spirit and scope of this invention.

What is claimed is:

1. A dental material holding and dispensing device comprising:
    a tray for containing a readily flowable dental material used by dentists for effecting various tooth restoration procedures, and
    an associated dental applicator for use therewith,
    said tray including a top planar surface,
    a depending side wall circumscribing said top planar surface forming a base,
    at least one material well formed in said top planar surface,
    said at least one material well having a frustroconical inlet portion defining an opening in said top planar surface, said inlet portion converging inwardly from said top planar surface, and a generally cylindrical portion having a closed bottom wall connected to said inlet portion whereby the depth and lateral width of said cylindrical portion are such that the surface tension of a readily flowable dental material contained in said cylindrical portion prohibits the readily flowable dental material from spilling out of said at least one material well if inverted, and
    said dental applicator having an elongated handle and an applicator end portion connected to one end of said elongated handle,
    said applicator end portion being sized so as to be received in said cylindrical portion of said at least one material well, said dental applicator being supportable within said cylindrical portion in a generally upright position to facilitate the grasping thereof by a user, and said cylindrical portion having a width not greater than three times the width of said applicator end portion.

2. A dental material holding and dispensing device comprising:

a tray for containing a readily flowable dental material used by dentists for effecting various tooth restoration procedures, and an associated dental applicator for use therewith, said tray including a top planar surface, said top planar surface including an uppermost planar portion and a lower planar portion, a depending side wall circumscribing said top planar surface forming a base, a plurality of material wells formed in said uppermost planar portion, each of said material wells having a frustroconical inlet portion defining an opening in said uppermost planar portion, said inlet portion converging inwardly from said uppermost planar portion, and a generally elongated cylindrical portion having a closed bottom wall connected to said inlet portion whereby the depth and lateral width of each of said material wells are such that the surface tension of a readily flowable dental material contained in each of said material wells prohibits the readily flowable dental material from spilling out of said material wells if inverted, and said dental applicator having an elongated handle and an applicator end portion connected to one end of said elongated handle, said applicator end portion being sized so as to be received in said cylindrical portion of each said material well, said dental applicator being supportable within said cylindrical portion in a generally upright position to facilitate the grasping thereof by a user, and said lower planar portion allowing for facilitating grasping of said tray by the user.

3. A dental material holding and dispensing device as defined in claim 2 wherein said cylindrical portion of each of said material wells defines a reservoir for the readily flowable dental material wherein the width of said cylindrical portion is substantially less than the axial length of said cylindrical portion.

4. A dental material holding and dispensing device as defined in claim 3 wherein the width of said cylindrical portion is not greater than three times the width of said applicator.

5. A readily disposable dental material and holding device comprising:

a tray for containing a readily flowable dental material selected from the group consisting of dental bonding agents, dental adhesives, dental etchings, acids, dental desensitizers, and dental solvents, an associated dental applicator for use therewith, said tray including a circular top planar surface, said circular top planar surface including an upper planar portion and a lower planar portion, said upper planar portion defining an arcuate portion of said circular top planar surface, a depending side wall circumscribing the periphery of said circular top planar surface, a plurality of circumferentially spaced apart material wells formed in said upper planar portion, each of said material wells including a frustroconical inlet portion defining an opening in said upper planar portion, said inlet portion converging inwardly from said upper planar portion, and a generally cylindrical portion terminating in a closed bottom wall connected to said inlet portion whereby the depth and lateral width of each said material well are such that the surface tension of a readily flowable dental material contained in each said material well prohibits the readily flowable dental material from spilling out of said material well if inverted, said associated dental applicator including an elongated handle and an applicator end portion connected to one end of said handle, said applicator end portion being sized so as to be received in said cylindrical portion, said dental applicator being supportable within said cylindrical portion in a generally upright position to facilitate the grasping thereof by a user, said cylindrical portion having a width not greater than three times the width of said applicator end portion, each said material well having a depth sufficient to minimize the exposure of the flowable dental material therein to ambient light, evaporation and, contamination.

6. A readily disposable dental material and holding device as defined in claim 5 wherein said tray is formed of an opaque, thin, plastic sheet.

* * * * *